(12) United States Patent
Konakahara

(10) Patent No.: US 7,609,378 B2
(45) Date of Patent: Oct. 27, 2009

(54) STRUCTURE FOR SUPPORTING SAMPLE TO BE SUBJECTED TO SURFACE ENHANCED VIBRATIONAL SPECTROSCOPIC ANALYSIS AND METHOD OF MANUFACTURING THE SAME

(75) Inventor: Kaoru Konakahara, Yokohama (JP)

(73) Assignee: Canon Kabushiki Kaisha, Tokyo (JP)

( * ) Notice: Subject to any disclaimer, the term of this patent is extended or adjusted under 35 U.S.C. 154(b) by 0 days.

(21) Appl. No.: 12/110,779

(22) Filed: Apr. 28, 2008

(65) Prior Publication Data

US 2008/0286526 A1    Nov. 20, 2008

(30) Foreign Application Priority Data

May 14, 2007    (JP)    ............... 2007-128268

(51) Int. Cl.
*G01J 3/44*    (2006.01)
(52) U.S. Cl. .................................... 356/301
(58) Field of Classification Search ............. 356/301, 356/244–246; 257/771, 763, E23.06–E23.07
See application file for complete search history.

(56) References Cited

U.S. PATENT DOCUMENTS

| | | | |
|---|---|---|---|
| 7,288,419 B2 | 10/2007 | Naya | |
| 7,351,588 B2 * | 4/2008 | Poponin | .............. 436/171 |
| 7,501,649 B2 * | 3/2009 | Naya et al. | .............. 257/9 |
| 2005/0105085 A1 | 5/2005 | Naya | |

FOREIGN PATENT DOCUMENTS

JP    2005-172569    6/2005

OTHER PUBLICATIONS

M. Fleischmann et al., "Raman Spectra of Pyridine Adsorbed at a Silver Electrode", Chemical Physics Letters, 1974, vol. 26, No. 2, pp. 163-166.
Y. Kobayashi et al., "Surface-Enhanced Resonance Raman Scattering Spectra of Meso-Substituted Porphines In Layered Structures Having CaF2/Porphine/Ag and CaF2/Ag/Porphine Configurations", J. Phys. Chem., 1985, vol. 89, No. 24, pp. 5174-5178.
S. Hayashi et al., "SERS Activity of Gas-evaporated Silver Particles", Solid State Communications, 1985, vol. 55, No. 12, pp. 1085-1088.
M. Futamata et al., "Local Electric Field and Scattering Cross Section of Ag Nanoparticles under Surface Plasmon Resonance by Finite Difference Time Domain Method", J. Phys. Chem. B, 2003, vol. 107, pp. 7607-7617.

* cited by examiner

*Primary Examiner*—Gregory J Toatley, Jr.
*Assistant Examiner*—Abdullahi Nur
(74) *Attorney, Agent, or Firm*—Fitzpatrick, Cella, Harper & Scinto

(57) ABSTRACT

A structure for supporting a sample to be subjected to a surface enhanced vibrational spectroscopic analysis includes a substrate, a ground film formed on the substrate, and a base formed on the ground film. The base includes a plurality of holes formed in a direction perpendicular to the substrate. Metal fine particles are exposed on inner surfaces of the holes formed in the base and on a surface of the base.

14 Claims, 8 Drawing Sheets

STRUCTURE FOR SUPPORTING SAMPLE TO BE SUBJECTED TO SURFACE ENHANCED VIBRATIONAL SPECTROSCOPIC ANALYSIS AND METHOD OF MANUFACTURING THE SAME

BACKGROUND OF THE INVENTION

1. Field of the Invention

The present invention relates to a structure for supporting a sample to be subjected to surface enhanced vibrational spectroscopic analysis and a method of manufacturing the structure, and more particularly, to a jig for surface enhanced vibrational spectroscopic analysis which is used for Raman spectroscopic analysis or infrared spectroscopic analysis and a method of manufacturing the jig.

2. Description of the Related Art

When a sample is irradiated with laser light, Raman scattered light which is different in frequency from original incident light is emitted from the sample together with Rayleigh scattered light which is equal in frequency to the original incident light. A Raman spectroscopic analysis method of analyzing the Raman scattered light is effective to determine a molecular structure or a bonding state of crystal.

However, there is a case where a sample such as an organic substance is sensitive to damage by laser light, so it is necessary to measure the sample at minimum laser intensity. Because the Raman scattered light intensity is extremely weak, when the sample is a thin film or when a measurement area is very small, it may be difficult to obtain the Raman spectrum. Therefore, there is required a technique for detecting the Raman scattered light whose intensity is extremely weak at high sensitivity even when the sample is irradiated with laser light at an intensity level at which the sample is not damaged.

An example of such technique is surface enhanced Raman scattering (SERS) (see Chem. Phys. Lett., Vol. 126, p. 163 (1974)). The SERS is a phenomenon in which the intensity of Raman scattered light from a sample of a monomolecular layer or a several-molecular layer which is deposited on a substrate on which a metal film made of a noble metal such as silver, gold, or copper (island-like film or fine particle film) is formed is $10^2$ to $10^6$ times larger than the intensity of Raman scattered light from a sample deposited on a substrate on which the metal film is not formed. It is also necessary to make the surface of the metal film rough. For example, a film which contains Si particles, Ag particles, or $CaF_2$ having a μm-size is formed as a ground film. When the metal film is formed on the ground film, the roughness of the surface of the metal film increases, so the SERS is observed at higher sensitivity (see J. Phys. Chem. 1985, 89, 5174-5178, and Solid State Communications, Vol. 55, No. 12, pp. 1085-1088, 1985). Even when the metal film is deposited on the surface of the sample, the SERS phenomenon is observed.

The same is expected even in the case of an infrared spectroscopic analysis method. When the sample is irradiated with infrared light, an infrared light having a frequency peculiar to the sample is absorbed thereinto. Information with respect to the molecular structure or environments of the molecules is obtained based on a frequency at an absorption position.

In recent years, a scanning probe microscope, a near-field microscope, an atomic force microscope, and the like have been under development. Therefore, the structure of each metal nano fine particle can be measured in nanoscale and simultaneously an interparticle distance can be controlled to detect Raman scattered light only from a specific particle to which an extremely small amount of molecules are absorbed.

For example, according to J. Phys. Chem. B, 2003, 107, 7607-7617, it has been reported that a local electric field intensity on the surface of a nano structure when the metal nano structure which produces sufficient SERS is irradiated with laser light is obtained by numeral calculation, thereby finding the metal nano structure which provides a very large enhanced intensity. When a local electric field intensity on an isolated spherical or elliptical metal nano particle is calculated, only an SERS enhanced intensity of $10^4$ to $10^5$ is obtained. In contrast to this, an enhanced intensity of $10^{10}$ or more which is equivalent to the sensitivity for a single molecule is obtained on a bonding area between spherical or elliptical nano particles at a suitable wavelength without depending on particle size. In other words, it is reported that the very large enhanced intensity equivalent to the sensitivity for a single molecule is obtained on the aggregation of the metal nano particles and the bonded particles.

It has been known that a structure in which metal fine particles are brought close to each other or bonded to each other is used for spectroscopic analysis of surface enhanced Raman scattering. For example, a metal is put into fine holes and exposed to shorten a distance between respective exposed metal fine particles to several nm. An analysis sample is deposited to the surfaces of the exposed metal fine particles and then irradiated with laser light. Therefore, surface enhanced Raman scattering measurement using an electromagnetic field generated between the metal fine particles to improve the sensitivity can be performed (see US 2005/0105085).

According to the conventional vibrational spectroscopic analysis method using the surface enhanced phenomenon, a Raman scattered light intensity or an absorption intensity is increased corresponding to an adsorption state of the sample on the metal film or an adsorption state of a metal on the surface of the sample. However, there is a problem that, when the sample is irradiated with incident light whose intensity is small, Raman scattered light of the sample or infrared absorption thereof cannot be measured in some cases.

It has been reported that a sufficient SERS intensity is obtained from a bonding area of an aggregate of metal nano particles and the vicinity thereof, or the like. In particular, in order to obtain the sufficient SERS intensity using metal nanostructures such as particles, the following is required. That is, the metal nanostructures are aggregated in high density or the metal nanostructures are disposed at an interval of approximately 0 nm to several nm (see US 2005/0105085). However, US 2005/0105085 describes that the metal nanostructures are only two-dimensionally disposed. In order to obtain the SERS intensity at high sensitivity, it is necessary to increase a surface area of a metal to which a measurement sample is deposited or the number of metal fine particles.

SUMMARY OF THE INVENTION

The present invention has been made in view of the two problems described above. An object of the present invention is to provide a structure for supporting a sample with which Raman scattered light or infrared absorption can be measured at high sensitivity, and a method of manufacturing the structure.

In order to attain the object, the present invention provides a structure for supporting a sample to be subjected to surface enhanced vibrational spectroscopic analysis, including: a substrate; a ground film formed on the substrate; and a base formed on the ground film, in which the base includes a plurality of holes formed in a direction perpendicular to the substrate and metal fine particles are exposed on inner surfaces of the holes formed in the base and on a surface of the base.

The present invention also provides a method of manufacturing a structure for supporting a sample to be subjected to surface enhanced vibrational spectroscopic analysis, at least including the steps of: forming a ground film on a substrate; forming, as a base, a film including metal fine particles on the ground film; and forming a plurality of holes in the base in a direction perpendicular to the substrate; in which the metal fine particles are exposed on inner surfaces of the holes formed in the base and on a surface of the base by the step of forming the film and the step of forming the holes.

According to the present invention, the plurality of holes are provided in the base to increase surface areas of exposed portions of the metal fine particles. Therefore, Raman scattered light or infrared absorption can be measured at high sensitivity. According to the present invention, a life of the structure for supporting the sample to be subjected to surface enhanced vibrational spectroscopic analysis can be lengthened.

Further features of the present invention will become apparent from the following description of exemplary embodiments with reference to the attached drawings.

BRIEF DESCRIPTION OF THE DRAWINGS

FIGS. 1A, 1B and 1C are schematic views illustrating structures for supporting a sample to be subjected to surface enhanced vibrational spectroscopic analysis according to the present invention, in which FIG. 1A illustrates the case where a base has a layered film in which a layer including metal fine particles and an Al layer (or Si layer) are alternately layered, FIG. 1B illustrates the case where the base has a Si layer in which the metal fine particles are dispersed, and FIG. 1C illustrates the case where exposed metal fine particles 14 are covered with a metal film 18.

FIGS. 2A, 2B and 2C are step diagrams illustrating an embodiment of a manufacturing method according to the present invention (case of the Al layer or Si layer), in which FIG. 2A illustrates a step of forming a ground film, FIG. 2B illustrates a step of forming the layered film, and FIG. 2C illustrates a step of forming fine holes 17.

FIGS. 3A, 3B, 3C and 3D are step diagrams illustrating another embodiment of a manufacturing method according to the present invention, in which FIG. 3A illustrates a step of forming the ground film, FIG. 3B illustrates a step of forming the layered film, FIG. 3C illustrates a step of performing heat treatment, and FIG. 3D illustrates a step of forming fine holes.

FIGS. 4A, 4B and 4C are step diagrams illustrating another embodiment of a manufacturing method according to the present invention (case of a (Al, Si, Ge) mixed layer), in which FIG. 4A illustrates a step of forming the ground film, FIG. 4B illustrates a step of forming an alternately layered thin film, and FIG. 4C illustrates a step of forming fine holes.

FIGS. 5A and 5B are schematic views illustrating a (Al, Si, Ge) mixed layer, in which FIG. 5A is a plan view and FIG. 5B is a cross sectional view along the line 5B-5B of FIG. 5A.

FIGS. 7A and 7B illustrate a step of forming a gold film by nonelectrolytic plating, in which FIG. 7A illustrates a state before plating and FIG. 7B illustrates a state after plating.

FIGS. 8A and 8B illustrate a step of increasing a hole diameter by etching, in which FIG. 8A illustrates a state before etching and FIG. 8B illustrates a state after etching.

DESCRIPTION OF THE EMBODIMENTS

Preferred embodiments of the present invention will now be described in detail in accordance with the accompanying drawings.

Figure 1A:
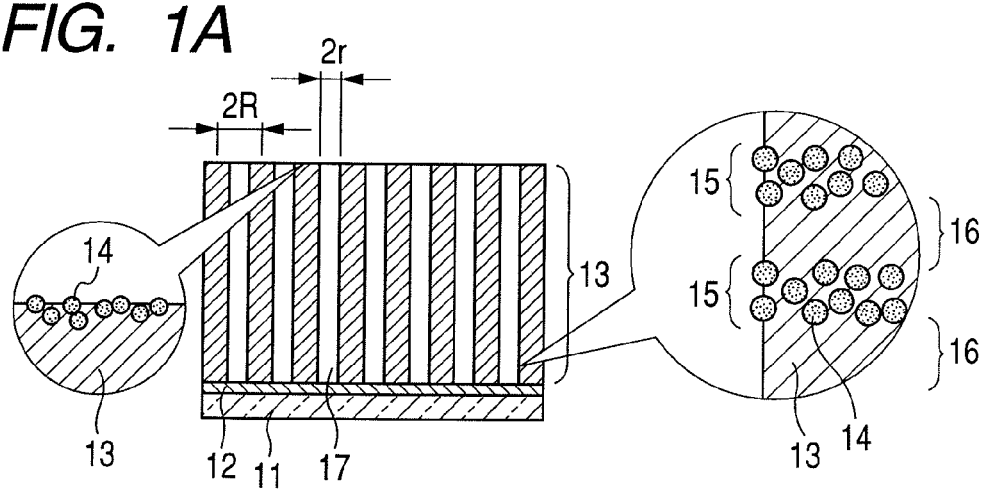
Figure 1B:
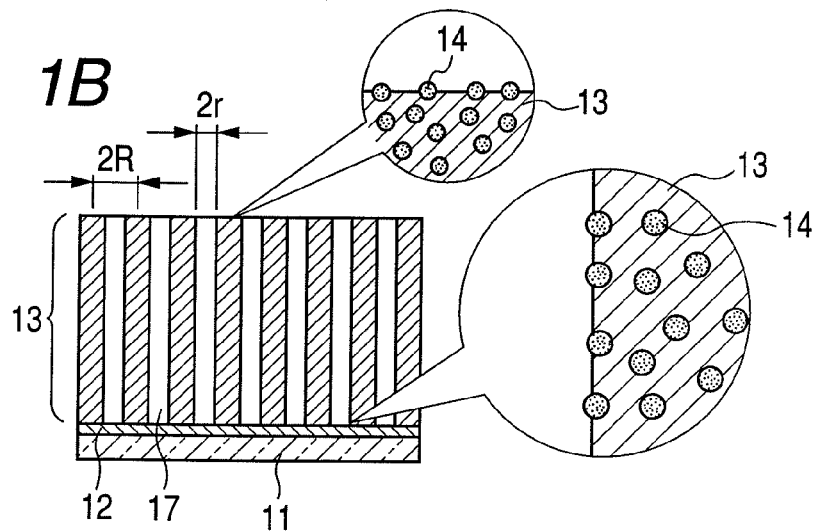
Figure 1C:
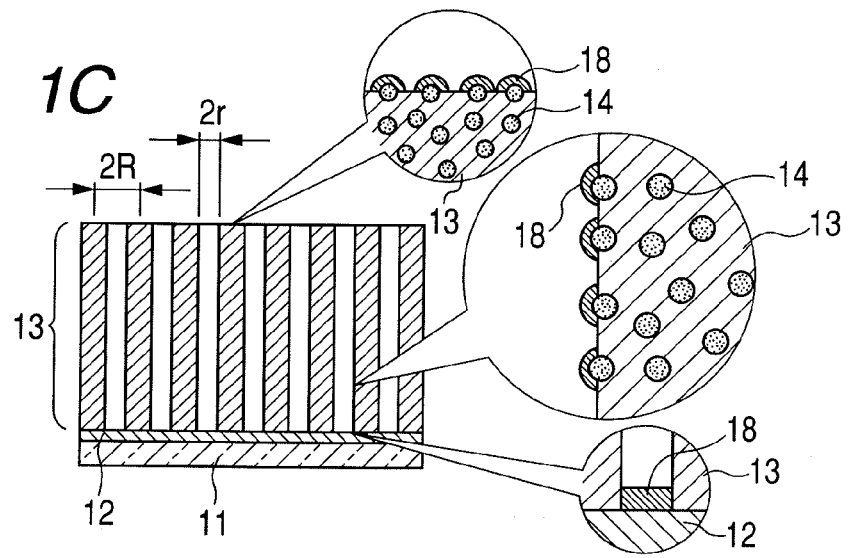

A structure for supporting a sample to be subjected to surface enhanced vibrational spectroscopic analysis (jig for surface enhanced vibrational spectroscopic analysis which is used for performing sampling and vibrational spectroscopic analysis) according to the present invention is described (FIGS. 1A to 1C).

As illustrated in FIG. 1A, a base 13 is formed on a substrate 11 on which a ground film 12 is provided and a large number of holes 17 are formed in the base 13 in a direction perpendicular to the surface of the substrate 11. The base 13 is a thin film in which a layer 15 including metal fine particles and a Si layer (or Al layer) 16 are alternately layered. Hereinafter, the layer 15 including the metal fine particles are referred to as a metal fine particle layer. Metal fine particles 14 of the metal fine particle layer 15 are exposed on inner surfaces (surface of the inside) of the holes 17 formed in the base 13 and on the surface of the base 13. Hereinafter, the inner surfaces of the holes 17 formed in the base 13 may be merely referred to as "inner surfaces of the holes 17" for the sake of convenience. Regions in which the metal fine particles are exposed in the base are enlarged in each of FIGS. 1A, 1B, and 1C. In this case, the metal fine particle layer 15 includes the metal fine particles 14 and Si. In other words, in the case where the film thickness of the metal fine particle layer layered on an Si layer is thin, when an Si thin film is subsequently formed on the thin metal fine particle layer, Si is deposited in the interspace between the metal fine particles 14. Therefore, as illustrated in FIG. 1A, the metal fine particle layer 15 includes the metal fine particles 14 and Si.

On the other hand, when the film thickness of the metal fine particle layer is sufficiently thick, a fine particle metal layer and an Si layer are alternately layered. In this case, after the layers are alternately layered, heat treatment is performed to diffuse the metal, with the result that the metal fine particles can be diffused into the base. When such heat treatment is performed, the metal fine particles 14 can be diffused throughout the base 13 as illustrated in FIG. 1B.

In FIG. 1B, the base 13 is formed on the substrate 11 on which the ground film 12 is provided and a large number of holes 17 are formed in the base 13 in the direction perpendicular to the surface of the substrate 11. A large number of metal fine particles 14 are dispersed in the base 13. Further, a large number of metal fine particles 14 are exposed on the inner surfaces of the holes 17 and on the surface of the base 13 (enlarged part of FIG. 1B).

In FIG. 1C, the base 13 is formed on the substrate 11 on which the ground film 12 is provided and a large number of holes 17 are formed in the base 13 in the direction perpendicular to the surface of the substrate 11. A large number of metal fine particles 14 are dispersed in the base 13. A large number of metal fine particles 14 are exposed on the inner surfaces of the holes 17 and on the surface of the base 13. A metal film 18 different from the metal fine particles 14 are formed so as to cover the exposed metal fine particles 14. The metal film 18 is not derived from the metal fine particles 14 but are formed by another manufacturing process.

The ground film 12 is desirably made of a metal having a catalytic activity, such as Ag, Au, Cu, Pt, Pd, and Cr. In particular, Au, Pt, or Pd is desirable. However, the metal not having the catalytic activity may be used. The ground film 12 is desirably a continuous film having flatness.

Figure 5A:
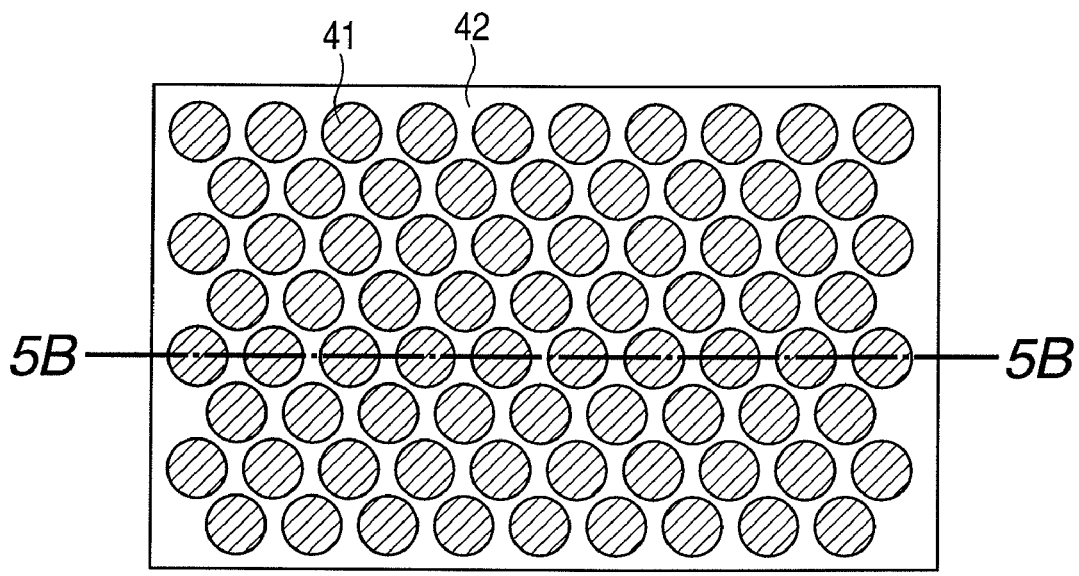
Figure 5B:
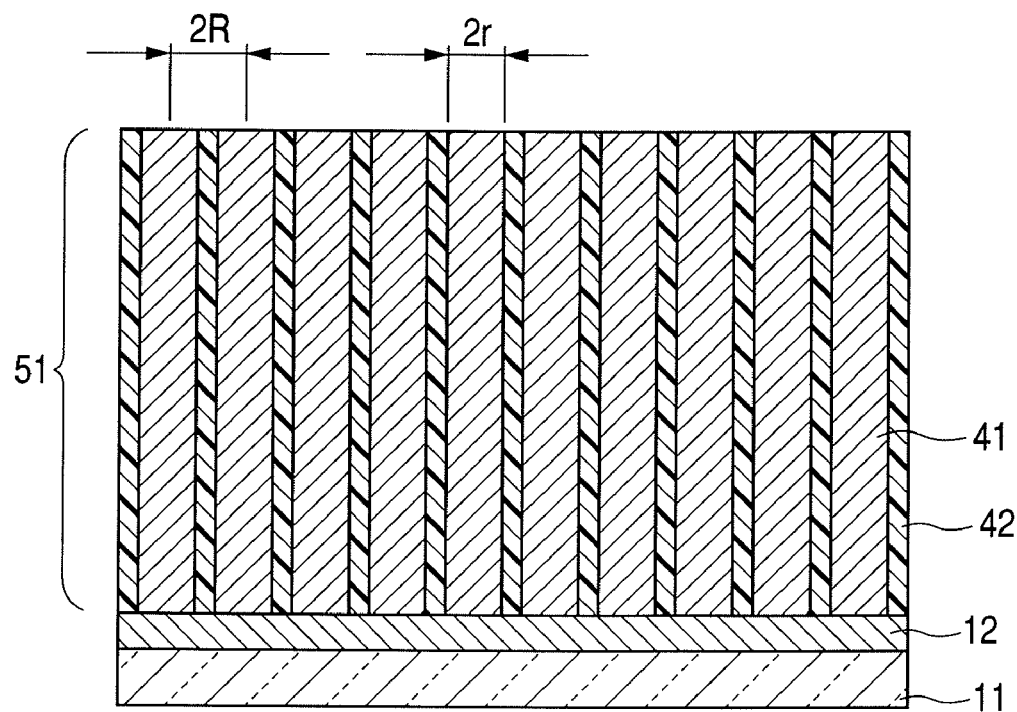

Further, the base 13 is desirably a thin film in which the metal fine particle layer 15 and the Si layer (or Al layer) 16 are alternately layered. Alternatively, the base 13 may be an Si film in which the metal fine particles 14 are dispersed. Further, the base 13 may be a (Al, Si, Ge) mixed film 51 having the following structure (FIGS. 5A and 5B). The structure includes columnar members 41 formed in the direction perpendicular to the surface of the substrate 11 with the ground film 12 and a matrix portion 42 provided so as to surround the side surfaces of the columnar members 41. The columnar members 41 contain Al as main ingredient. The matrix portion 42 contains any one of Si, Ge, and SiGe as main ingredient.

Further, the holes 17 may be holes which reach the ground film 12 or holes which do not reach the ground film 12.

From the experimental result, the diameter $2r$ of the holes is desirably 1 nm to 1 μm and the center-to-center distance $2R$ therebetween is desirably 3 nm to 1.5 μm. The aspect ratio of the holes is desirably equal to or larger than 2 and the length (depth) thereof is not limited. The aspect ratio as used herein is the ratio of the depth of the holes 17 to the diameter thereof.

The material of the metal fine particles 14 is desirably any one of Au, Ag, Pd, and Pt and the particle size thereof is desirably 1 nm to 30 nm. This is because an SERS phenomenon relatively easily occurs in the particle size range. The interspace distance between the metal fine particles 14 dispersed into the base 13 and the interspace distance between the exposed metal fine particles 14 is desirably 0 nm to 100 nm, particularly desirably 0 nm to 50 nm. This is because the SERS phenomenon relatively easily occurs in these interspace distance ranges. The metal fine particles 14 may be a mixture of Si and a metal, such as $M_xSi_{1-x}$ ($0 \leq X \leq 1$, M is any one of Au, Ag, Pd, and Pt). The "interspace distance" means a shortest distance between the particle surfaces of two adjacent metal fine particles.

The metal fine particle layer 15 is desirably a layer including a plurality of metal fine particles 14 which are bonded to each other or brought close to each other. In order to easily cause an SERS phenomenon, a desirable film thickness of the metal fine particle layer 15 is 1 nm to 100 nm. This film thickness range is suitable to control the distance between metal particles. The interspace distance between the metal fine particles 14 close to each other is desirably 0 nm to 100 nm, particularly desirably 0 nm to 50 nm. The case where the interspace distance is 0 nm indicates a state in which the metal fine particles are in contact with each other. A desirable particle size of the metal fine particle layer 15 is 1 nm to 30 nm. When the interspace distance and the particle size are set in the above-mentioned ranges, the SERS phenomenon can be relatively easily caused.

The Si layer 16, the Al layer 16, or the (Al, Si, Ge) mixed film 51 desirably has a film thickness of 1 nm to 100 nm. This is because the metal fine particles are easily dispersed.

The metal film 18 is desirably made of any one of Au, Pt, and Pd. The film thickness of the metal film 18 is desirably 1 nm to 30 nm.

By dispersing the metal fine particles as illustrated in FIG. 1B, the number of metal fine particles exposed on the inner surfaces of the holes 17 can be increased more than in the case of FIG. 1A. As a result, higher-sensitive analysis can be realized.

By covering the metal fine particles with the metal film as illustrated in FIG. 1C, the distance between the exposed metal fine particles can be shortened. Therefore, the intensity of an electric field generated in the interspace is further increased, thereby improving the sensitivity.

Next, a method of manufacturing the structure for supporting the sample to be subjected to surface enhanced vibrational spectroscopic analysis according to the present invention is described.

The manufacturing method according to the present invention is characterized by exposing, on the inner surfaces of the holes 17 formed in the base 13 or the surfaces of the base 13, a large number of metal fine particles 14 or a large number of metal fine particles 14 whose surfaces are covered with the metal film 18. The manufacturing method includes a step of forming the holes 17 in the base 13 formed on the substrate 11 on which the ground film 12 is provided in the direction perpendicular to the surface of the substrate 11. Alternatively, the manufacturing method includes a step of dispersing the metal fine particles 14 in the base 13 formed on the substrate 11 on which the ground film 12 is provided and forming the holes 17 in the direction perpendicular to the surface of the substrate 11. Alternatively, the manufacturing method further includes a step of forming the metal films 18 on the surfaces of the exposed metal fine particles 14.

A method of manufacturing the structure illustrated in FIG. 1A is described in detail below. A thin film which corresponds to the base 13 and is formed by alternately layering the metal fine particle layers 15 and the Si layer (or Al layer) 16 is subjected to anodic oxidation. The thin film is hereinafter referred to as a layered film 21. An example of the manufacturing method according to the present invention in this case is described in the following order of Step [a] to Step [c] (see FIGS. 2A to 2C).

Figure 2A:
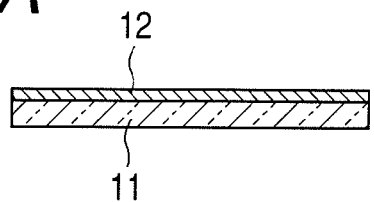

[a] Step of Forming Ground Film 12 (FIG. 2A)

In order to perform anodic oxidation, it is necessary to form the ground film 12 made of metal on the substrate 11. The ground film 12 is desirably of a metal which is not dissolved by an electrolytic solution which is acid or alkali. The metal is desirably a noble metal such as Pd, Pt, Ag, Au, Rh, and Ir. The film thickness of the ground film 12 may be controlled as desired. The film thickness is desirably equal to or less than 100 nm, particularly desirably equal to or less than 20 nm. Examples of the method of forming the ground film 12 include a sol-gel method, a vapor deposition method, and a sputtering method. In the present invention, the sputtering method is employed to form the continuous ground film 12 whose film thickness is equal to or less than 20 nm.

Figure 2B:
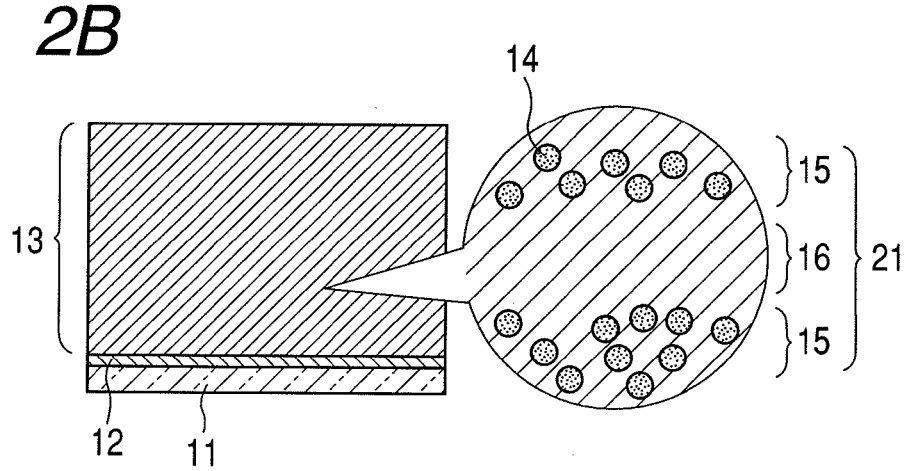

[b] Step of Forming Layered Film 21 (FIG. 2B)

Examples of a method of forming the layered film 21 include a sol-gel method, a vapor deposition method, and a sputtering method. In the present invention, the sputtering method is employed.

The metal fine particle layer 15 and the Si layer (or Al layer) 16, each of which has a desirable film thickness can be alternately formed. For example, the Si layer (or Al layer) 16 having a film thickness of 20 nm and the metal fine particle layer 15 having a film thickness of 10 nm can be continuously and alternately layered on the ground film 12 formed on the substrate 11 to obtain the layered film 21 whose film thickness is 240 nm. The layered film 21 can be formed at a desirable film thickness. With respect to formation conditions of the layered film, an inert gas such as Ar or He may be used as an atmospheric gas and the layers may be layered in high vacuum.

When the film thickness of the metal fine particle layer 15 is approximately 10 nm, a Si thin film is subsequently formed on the metal fine particles 14, wherein Si is deposited in the interspace between the metal fine particles 14. Therefore, as illustrated in FIG. 2B, the metal fine particle layer 15 includes the metal fine particles 14 and Si.

Figure 2C:
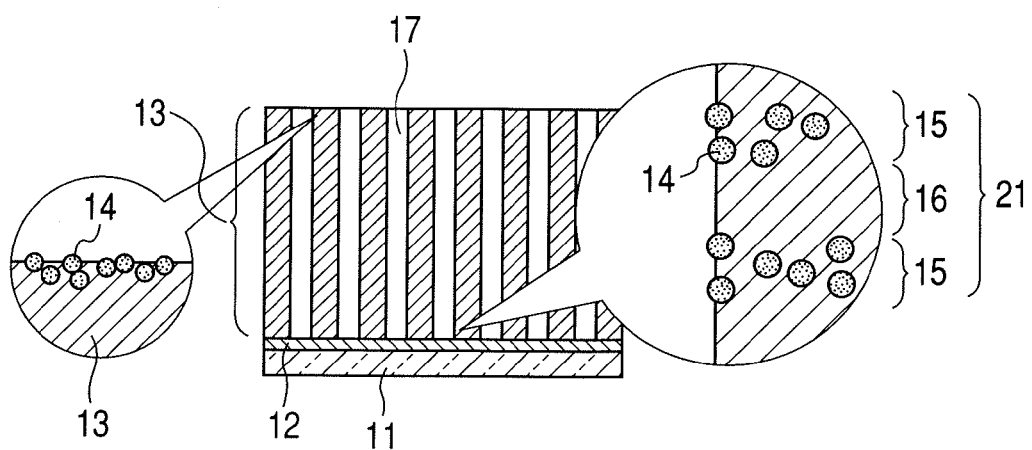

[c] Step of Forming Holes 17 (FIG. 2C)

Hereinafter, the anodic oxidation of the layered film 21 is described. First, the anodic oxidation of Si or an Si alloy is described. In the anodic oxidation of Si or the Si alloy, the average diameter $2r$ of the holes 17 can be controlled in a range of 1 nm to 500 nm. The center-to-center distance $2R$ between the holes 17 is equal to or larger than 3 nm and can be controlled in a range between a value slightly larger than the average diameter $2r$ of the holes 17 and approximately 1 μm. For example, a mixture of hydrofluoric acid aqueous solution (1 w % to 50 w %) and ethanol aqueous solution (10 w % to 99 w %) may be used for the anodic oxidation of Si or the Si alloy. The mixing ratio between hydrofluoric acid and ethanol may be set to a desirable numeral value, and the mixture ratio is desirably 1:2 to 2:1. The current to be applied may be 1 mA/cm$^2$ to 300 mA/cm$^2$. The temperature of the electrolytic solution may be 10° C. to 50° C. The diameter of the holes 17 formed by the anodic oxidation is changed by changes in resistivity of the Si material and doping amount of an impurity such as P or S (which imparts n-type or p-type). Therefore, in order to form the holes 17 having a desirable diameter, an Si target having suitable resistivity and doping amount may be selected. The average diameter $2r$ of the holes 17 can be increased by etching with a solution containing phosphoric acid after the anodic oxidation.

The anodic oxidation of Al or an Al alloy is described. In the anodic oxidation of Al or the Al alloy, the average diameter $2r$ of the holes 17 can be controlled in a range of 5 nm to 500 nm. The center-to-center distance $2R$ between the holes 17 is equal to or larger than 10 nm and can be controlled in a range between a value slightly larger than the average diameter $2r$ of the holes 17 and approximately 1 μm. An electrolytic solution containing an acid such as oxalic acid, phosphoric acid, sulfuric acid, or chromic acid can be employed for the anodic oxidation of Al or the Al alloy.

In particular, a sulfuric acid bath is desirably used to form the holes 17 at fine intervals, a phosphoric acid bath is desirably used to form the holes 17 at relatively large intervals, and an oxalic acid bath is desirably used to form the holes 17 at intermediate intervals. The average diameter $2r$ of the holes 17 can be increased by conducting etching in a solution containing an acid such as phosphoric acid or an alkali after the anodic oxidation.

Next, a method of manufacturing the structure illustrated in FIG. 1B is described in detail below. The thin film (layered film) 21 which corresponds to the base 13 and is formed by alternately layering the metal fine particle layer 15 and the Si layer 16 is subjected to heat treatment and then subjected to anodic oxidation. An example of the manufacturing method according to the present invention in such a case is described in the following order of Step [a] to Step [d] (FIGS. 3A to 3D).

Figure 3A:
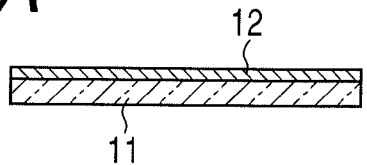

[a] Step of Forming Ground Film 12 (FIG. 3A)

The same operation as described with reference to FIG. 2A is performed.

Figure 3B:
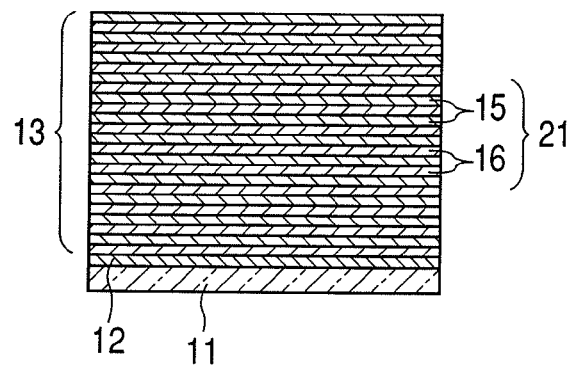

[b] Step of Forming Layered Film 21 (FIG. 3B)

Examples of a method of forming the layered film 21 include a sol-gel method, a vapor deposition method, and a sputtering method. In the present invention, the sputtering method is employed.

The metal fine particle layer 15 and the Si layer 16, each of which has a desirable film thickness can be alternately formed. The film thickness of the Si layer 16 is desirably equal to or less than the film thickness of the metal fine particle layer 15. For example, the Si layer 16 having a film thickness of 20 nm and the metal fine particle layer 15 having a film thickness of 30 nm are alternately layered on the ground film 12 formed on the substrate 11 to form the layered film 21 whose film thickness is 220 nm. Then, the metal fine particle layer 15 is formed at a film thickness of 10 nm. The layered film 21 can be formed at a desirable film thickness.

Any one of Au, Ag, Pd, and Pt may be used as a material of the metal fine particle layer 15. A mixture of Si and a metal, such as $M_xSi_{1-x}$ ($0 \leq X \leq 1$, M is any one of Au, Ag, Pd, and Pt) may also be used as the material. In the present invention, for example, the metal fine particle layer 15 made of $Au_{0.4}Si_{0.6}$ and the Si layers 16 may be alternately formed by a sputtering method using an Au target and an Si target.

With respect to the formation conditions of the layered film, an inert gas such as Ar and He may be used as an atmospheric gas and the alternate layer formation may be performed in high vacuum. In the present invention, the pressure of the inert gas is desirably 1 mTorr to 100 mTorr. The layer formation is desirably performed at a deposition rate of 0.3 angstroms/second to 1.1 angstroms/second.

Figure 3C:
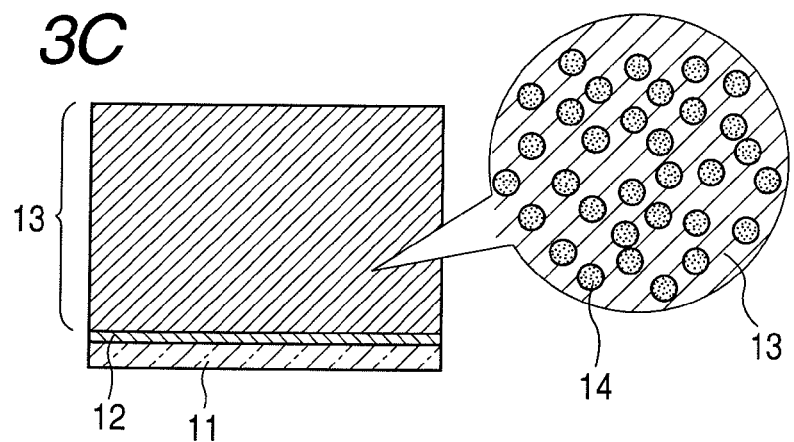

[c] Heat Treatment Step (FIG. 3C)

In a heat treatment step, the layered film 21 formed in Step [b] is desirably subjected to heat treatment in vacuum or in an inert gas atmosphere such as an Ar atmosphere and a He atmosphere. In particular, it is desirable to perform the heat treatment in an inert gas atmosphere at an atmospheric pressure.

The heat treatment temperature and the heat treatment time may be controlled as desired. In particular, it is desirable to select a heat treatment condition which is suitable to sufficiently disperse the metal fine particles 14 based on the film thickness ratio between the Si layer 16 and the metal fine particle layer 15, thereby performing the heat treatment. In the present invention, when the metal fine particle layer 15 made of $Au_{0.4}Si_{0.6}$ and the Si layer 16 are alternately layered, the heat treatment temperature is desirably 200° C. to 300° C. and the heat treatment time is desirably 30 minutes to 2 hours.

Figure 3D:
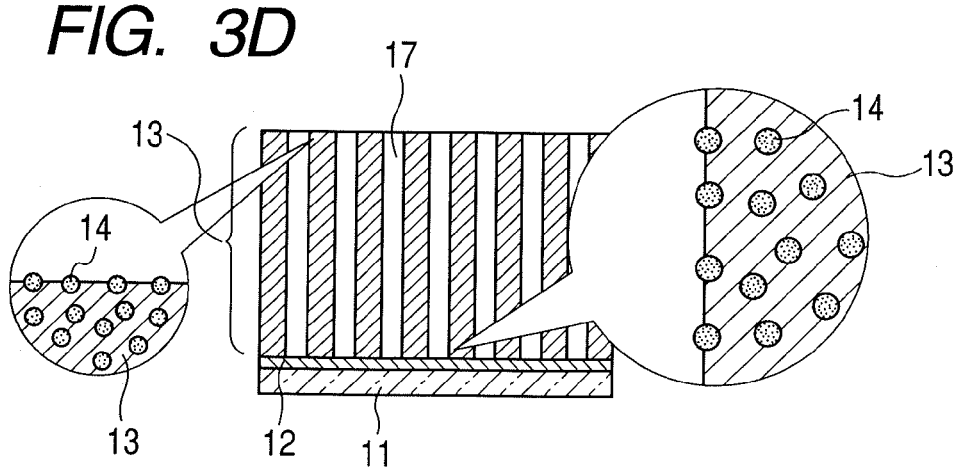

[d] Step of Forming Fine Holes 17 (FIG. 3D)

As in the case of FIG. 2C, the layered film 21 is desirably subjected to anodic oxidation. The same anodic oxidation condition as in the case of FIG. 2C is used.

Another method of manufacturing the structure illustrated in FIG. 1A is as follows. In the present invention, the columnar members 41 containing Al as a main ingredient are formed in the base 13 in the direction perpendicular to the surface of the substrate 11 with the ground film 12. The structure including the matrix portion 42 containing any one of Si, Ge, and SiGe as a main ingredient is formed so as to surround the side surfaces of the columnar members 41 containing Al as a main ingredient. In the matrix portion 42, the (Al, Si, Ge) mixed layer 16 and the metal fine particle layer 15 are alternately layered. Then, the resultant substrate 11 is etched. The manufacturing method is described below (see FIGS. 4A to 4C).

The (Al, Si, Ge) mixed layer 16 is any one of a (Si, Al)O$_X$ mixed layer ($0 \leq X \leq 2$), a (Ge, Al)O$_X$ mixed layer ($0 \leq X \leq 2$), and a (Si, Ge, Al)O$_X$ mixed layer ($0 \leq X \leq 2$).

The (Si, Al)O$_X$ mixed layer ($0 \leq X \leq 2$) in the case of X=0 is described. In other words, the (Si, Al) mixed layer 16 is provided. The columnar members 41 containing Al as a main ingredient are surrounded by a region containing Si as a main ingredient, that is, by the matrix portion 42. The (Si, Al) mixed layer 16 has such a feature that it contains Si at a ratio of 20 at % to 70 at % to the total amount of Al and Si. This ratio is a ratio of Si to the total amount of Al and Si which are contained in the (Al, Si) mixed layer 16. The ratio is desirably 25 at % to 65 at %, more desirably 30 at % to 60 at %. The unit symbol "at %" related to the ratio between Al and Si indicates a ratio of number of atom between Si and Al. The ratio is expressed by "atom %" or at % and corresponds to a value obtained by quantitative analysis on Si and Al which are contained in the (Al, Si) mixed layer 51 using, for example, an inductively coupled plasma emission spectroscopy (ICP method).

In the case of the (Al, Ge) mixed layer or the case of the (Al, Si, Ge) mixed layer, Ge or SiGe can be used instead of Si in the case of the (Al, Si) mixed layer 51.

FIGS. 5A and 5B illustrate the structure in which the (Al, Si, Ge) mixed layer 51 is formed on the substrate 11 with the ground film 12. In FIGS. 5A and 5B, the columnar members 41, the matrix portion 42 containing Si as a main ingredient, the ground film 12, and the substrate 11 are illustrated. In the (Al, Si, Ge) mixed layer 51, a plurality of columnar members 41 are dispersed in the matrix portion 42. The average diameter (diameter in the case of a circular planar shape) $2r$ of the columnar members 41 (FIG. 5B) can be controlled mainly based on a formation condition of the (Al, Si, Ge) mixed layer 51. The average diameter $2r$ is 0.5 nm to 20 nm, desirably 1 nm to 15 nm. In the case of an elliptical planar shape, the average diameter within the longest outer diameter may be used. The average diameter is, for example, a value derived by directly measuring a columnar portion image observed on an actual SEM photograph or by image-processing of the SEM photograph using a computer. Note that, although a lower limit of the average diameter of the thin film depends on a type of a device for which the thin film is used or a kind of treatment performed on the thin film, a practical lower limit value of the average diameter thereof is equal to or larger than 1 nm, desirably equal to or larger than several nm. The center-to-center distance $2R$ between the columnar members 41 (FIG. 5B) is equal to or smaller than 30 nm, desirably 3 nm to 20 nm.

The (Al, Si, Ge) mixed layer 51 is desirably a film-shaped structure. The columnar members 41 are desirably dispersed in the matrix portion 42 so as to be perpendicular to the ground film 12 and the substrate 11. The film thickness of the (Al, Si, Ge) mixed layer 51 is not particularly limited. The film thickness can be set in a range of 1 nm to 100 μm.

Figure 4A:
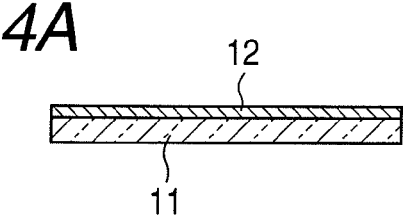
Figure 4B:
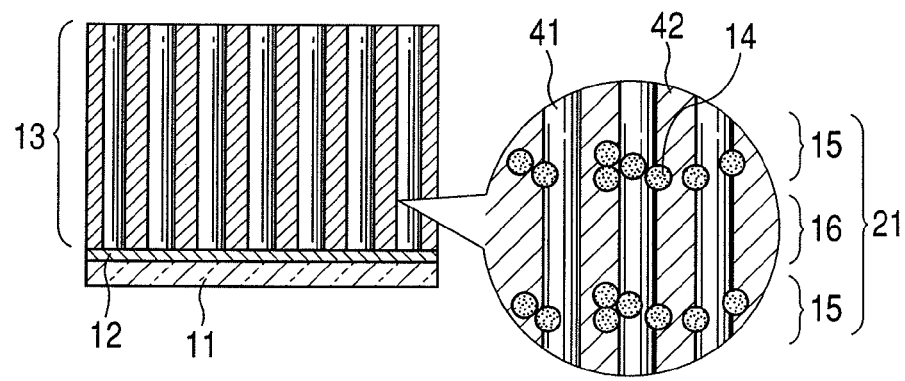
Figure 4C:
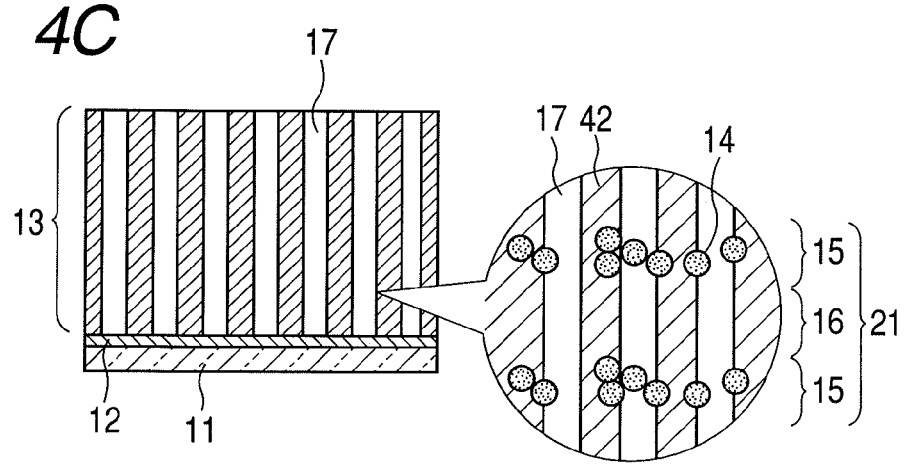

Next, an embodiment of the method of manufacturing the structure according to the present invention as illustrated in FIGS. 4A to 4C is described. This method is a method of alternately layering the (Al, Si, Ge) mixed layer 16 (for example, (Si, Al)O$_X$ mixed layer 16 (0≦X≦2) is employed) and the metal fine particle layer 15 and etching the resultant substrate or performing heat treatment on the substrate after etching.

The mixed layer 16 can be produced using a method of forming films in a non-equilibrium state. The film formation method in the present invention is desirably a sputtering method. It is possible to apply a film formation method of forming substrates in a non-equilibrium state, such as a resistance heating vapor deposition method or an electron beam (EB) vapor deposition method.

An example is described in the following order of Step [a] to Step [e] (FIGS. 4A to 4C).

[a] Step of forming Ground Film 12 (FIG. 4A) is the same as described in FIG. 2A.

[b] Step of forming Thin Film in which (Al, Si) Mixed Layer 16 ((Si, Al)O$_X$ Mixed Layer 16 (X=0)) and Metal Fine Particle Layer 15 are alternately layered (FIG. 4B).

The (Al, Si) mixed layer 16 and the metal fine particle layer 15 are alternately layered on the ground film 12 formed in Step [a]. Examples of the method of forming the layered film 21 include a sol-gel method, a vapor deposition method, and a sputtering method. In the present invention, the sputtering method is employed.

The metal fine particle layer 15 and the (Al, Si) mixed layer 16, each of which has a desirable film thickness can be alternately formed. For example, the (Al, Si) mixed layer 16 having a film thickness of 20 nm and the metal fine particle layer 15 having a film thickness of 10 nm can be alternately layered on the ground film 12 to form the layered film 21 whose film thickness is 210 nm. Finally, the metal fine particle layer 15 is formed at a film thickness of 5 nm. The layered film 21 can be formed at a desirable film thickness.

The metal fine particle layer 15 is desirably made of any of Au, Ag, Pd, and Pt.

With respect to formation conditions of the layered film, an inert gas such as Ar and He may be used as an atmospheric gas and the layers may be alternately layered in high vacuum. In particular, in the present invention, the pressure of the inert gas is desirably 1 mTorr to 100 mTorr.

A method of forming the (Al, Si) mixed layer 16 is described in detail.

Figure 6:
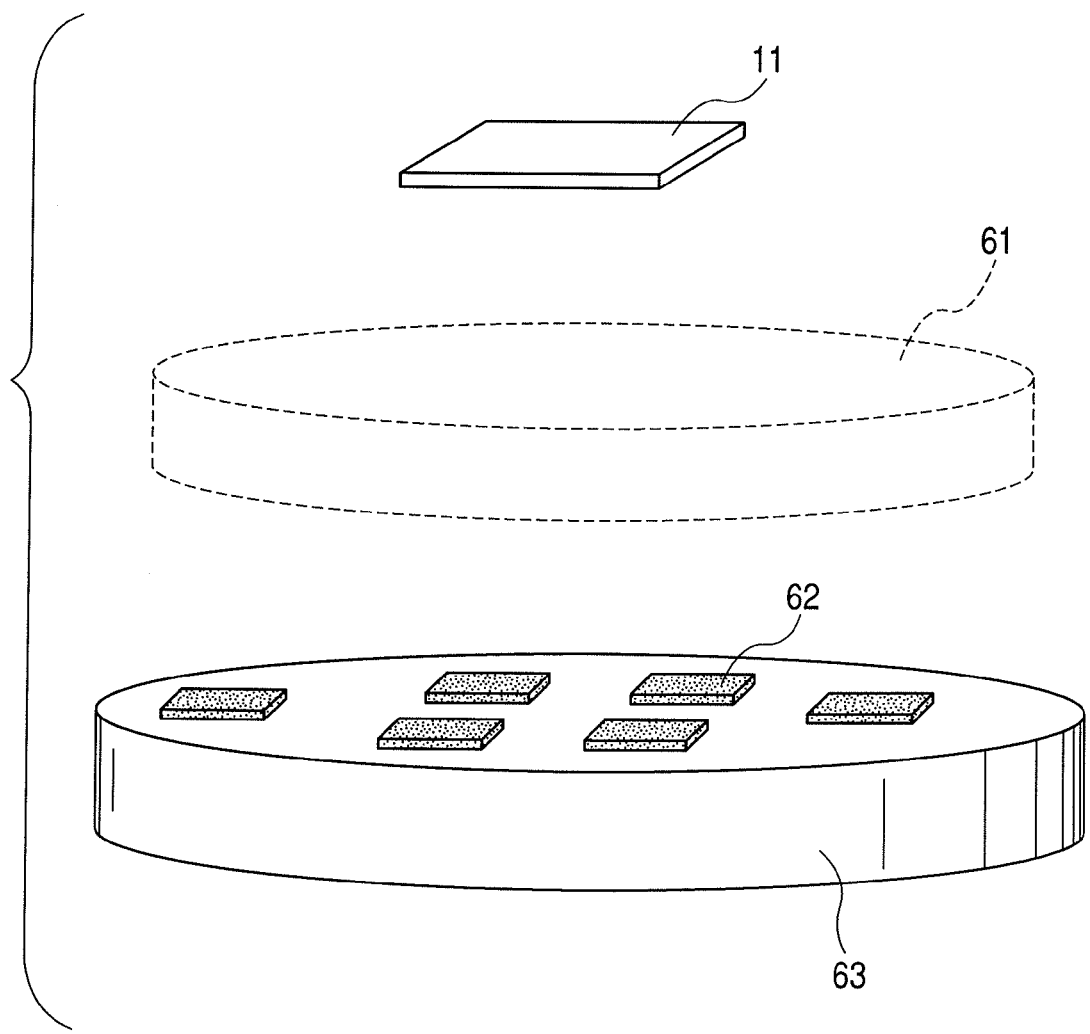
FIG. 6 is a schematic view illustrating a step of forming a (Al, Si, Ge) mixed layer (case of sputtering method).

As illustrated in FIG. 6, the (Al, Si) mixed layer 16 is formed on the ground film 12 by a sputtering method. As illustrated in FIG. 6, a Si chip 62 is arranged on an Al target 63. Although a plurality of Si chips 62 are separately arranged in FIG. 6, the present invention is not limited to this case. The number of chips may be one if desirable film formation can be performed. Note that, in order to uniformly disperse the columnar members 41 uniformly containing Al in the matrix portion 42 containing Si as a main ingredient, the Si chips 62 are desirably symmetrically arranged on the Al target 63. An AlSi sintered material produced by baking predetermined amounts of Al and Si powders can be used as a target material for film formation. A method of performing simultaneous sputtering with both an Al target and Si target which are separately prepared may be used.

The amount of Si contained in the formed mixed layer is 20 at % to 70 at % of the total amount of Al and Si, desirably 25 at % to 65 at % thereof, more desirably 30 at % to 60 at % thereof. When the amount of Si is within such a range, the (Al, Si) mixed layer 16 in which the columnar members 41 containing Al as a main ingredient are dispersed in the matrix portion 42 containing Si as a main ingredient is obtained. A desirable substrate temperature is equal to or smaller than 200° C.

When the (Al, Si) mixed layer 16 is formed using such a method, Al and Si become an eutectic structure in a metastable state, so Al forms nanostructures of a several-nm-level (columnar members 41) in the matrix portion 42 containing Si. The formed nanostructures separate in a self organizing manner. At this time, each of the columnar members 41 containing Al has a substantially cylindrical shape. The hole diameter is 1 nm to 15 nm and the center-to-center distance is 2 nm to 30 μm.

The amount of Si of the (Al, Si) mixed layer 16 can be controlled by, for example, adjusting the number of Si chips 62 placed on the Al target 63. When film formation is performed in a nonequilibrium state, in particular, in the case of a sputtering method, a desirable internal pressure of a reaction apparatus to which an Ar gas is introduced is 1 mTorr to 10 mTorr. Desirable power for forming plasma in the case of a 4-inch target is approximately 150 W to 1000 W. However, the present invention is not particularly limited to the pressure and the power. The film formation may be performed at pressure and power that are necessary to stably form an Ar plasma 61.

[c] Step of Forming Fine Holes 17 (FIG. 4C)

Only Al regions (regions corresponding to the columnar members 41 containing Al as a main ingredient) of the layered film 21 are selectively etched. As a result, only the matrix portion 42 which has the holes 17 and contains Si as a main ingredient is left, thereby forming a porous material. The (Al, Si) mixed layer 16 may be oxidized on each etching, so the (Si, Al)$O_X$ porous material 16 ($0 \leq X \leq 2$) is formed. Note that, in the (Si, Al)$O_X$ porous material 16 ($0 \leq X \leq 2$), the center-to-center distance 2R between the holes 17 is equal to or smaller than 30 nm and the average diameter 2r thereof is equal to or smaller than 20 nm. The average diameter 2r of the holes 17 is desirably 1 nm to 15 nm and the center-to-center distance 2R therebetween is desirably 3 nm to 20 nm. The length (depth) of the holes 17 is in a range of 1 nm to 100 µm.

A solution used for etching is, for example, an acid solution by which Al is dissolved and Si is hardly dissolved, such as a phosphoric acid solution, a sulfuric acid solution, a hydrochloric acid solution, or a chromic acid solution. An alkali solution such as a sodium hydroxide solution or ammonia water can be used if it is not inconvenient to form the holes 17 by etching. The present invention is not particularly limited by the type of acid and the type of alkali. A mixture of several types of acid solutions or a mixture of several types of alkali solutions may be used. Etching conditions including a solution temperature, a concentration, and a time can be set as appropriate based on the formed (Si, Al)$O_X$ porous material 16 ($0 \leq X \leq 2$).

In Step [b] and Step [c], when Ge or SiGe is used instead of Si in the case of the (Al, Si) mixed layer 16, the (Al, Ge) mixed layer or the (Al, Si, Ge) layer can be also formed.

Hereinafter, a method of manufacturing the structure illustrated in FIG. 1C is described in detail.

Figure 7A:
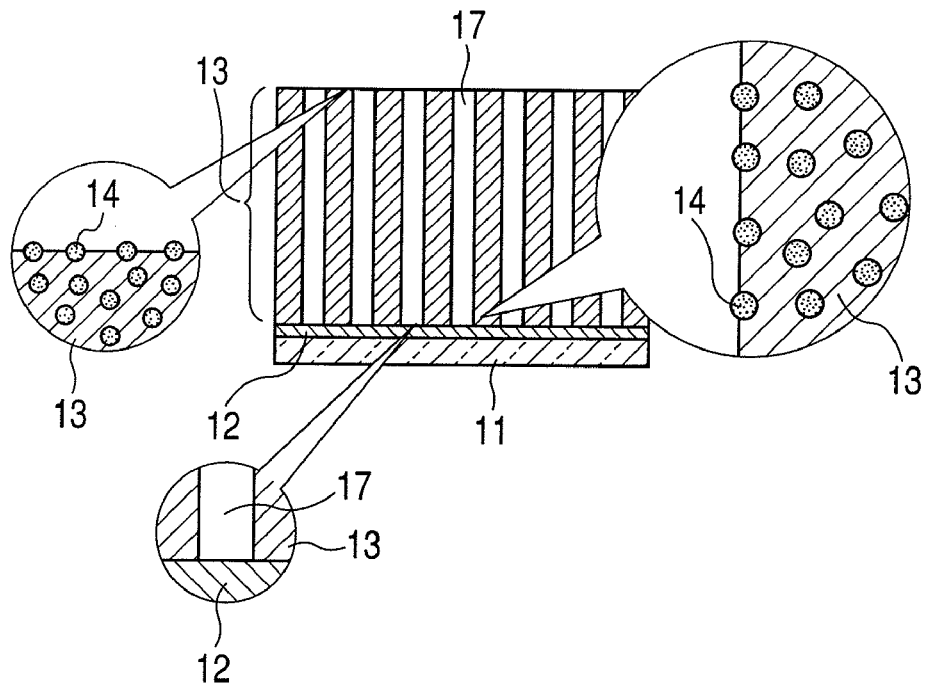
Figure 7B:
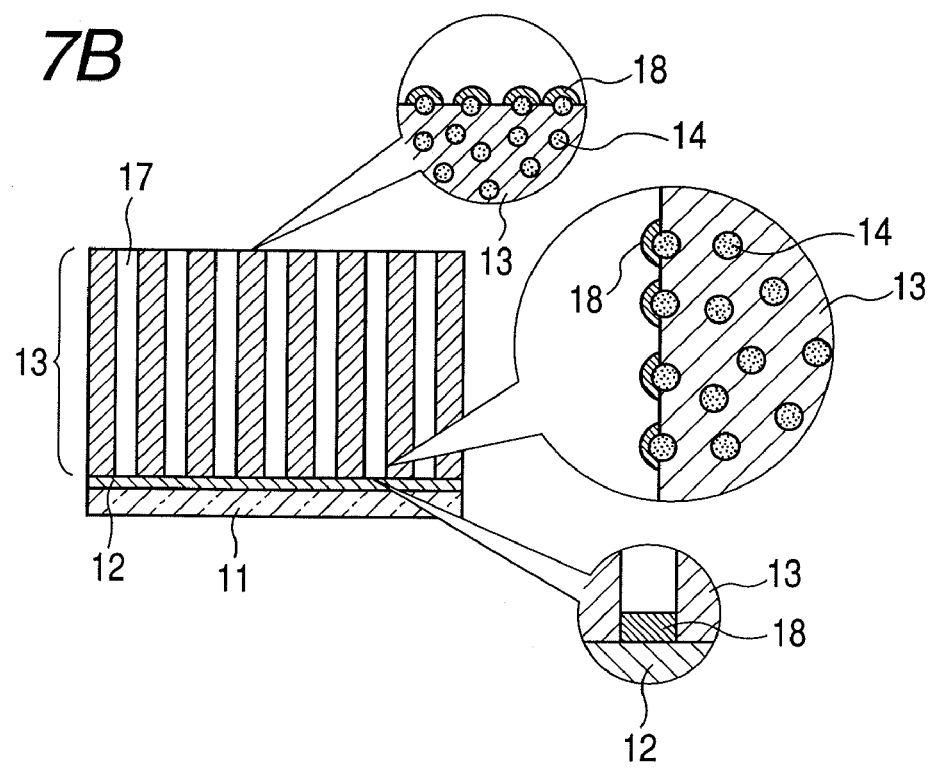

An example of a manufacturing method using nonelectrolytic plating for the step of forming the metal film 18 on the surfaces of the exposed metal fine particles 14 is described (see FIGS. 7A and 7B).

As illustrated in FIG. 1A or 1B, the structure is manufactured in which the metal fine particles 14 are exposed on the inner surfaces of the holes 17 or the surface of the base 13 (FIG. 7A) Subsequently, the manufactured structure is immersed in a nonelectrolytic plating bath, so the metal film 18 can be formed on the exposed portions of the metal fine particles 14 (FIG. 7B) The interspace distance between the metal fine particles 14 whose surfaces are covered with the metal film 18 is desirably 0 nm to 50 nm, more desirably 0 nm to 3 nm.

A desirable material of the metal film 18 formed by nonelectrolytic plating is a noble metal such as Au or Pt. Conditions for forming the metal film 18 by nonelectrolytic plating include a combination of types of components contained in the plating bath, such as a metal salt, a reducing agent, a complexing agent, and a pH adjuster, respective concentrations, a plating bath temperature, an agitation speed, a pH adjustment, and a time for which the substrate (structure) is immersed in the nonelectrolytic plating bath. When the conditions are controlled, the metal film 18 can be formed at a desirable film thickness.

The plating bath used for nonelectrolytic plating contains, as a main ingredients, a salt containing a metal to be precipitated, that is, a metal salt, and a reducing agent for providing electrons to precipitate metal ions as metals, such as hydrazine, sodium hypophosphite, or dimethylamine borane. The plating bath also contains an addition agent necessary to prevent metals from being precipitated therein, that is, a complexing agent. When a complexing agent such as sodium citrate or sodium tartrate is added, metal ions can form metal complexes to maintain their condition. Therefore, it is also desirable to add the complexing agent. Although a pH adjuster including a basic compound such as sodium hydroxide or ammonia water significantly affects a plating rate, reduction efficiency, a state of a plating coating, it is desirable to add the pH adjuster in order to stabilize the pH of the nonelectrolytic plating bath. The pH of the nonelectrolytic plating bath depends on the type of nonelectrolytic plating. When the pH of the nonelectrolytic plating bath is within a pH range in which the base is not dissolved, a nonelectrolytic plating bath which is acid or alkali may be used.

Hereinafter, a vibrational spectroscopic analysis method using the structure serving as the jig for surface enhanced vibrational spectroscopic analysis according to the present invention is described.

The jig for surface enhanced vibrational spectroscopic analysis according to the present invention is classified into two types, a jig for surface enhanced Raman spectroscopic analysis and a jig for surface enhanced infrared spectroscopic analysis.

Various methods including a method of causing a sample of a mono- or multi-molecular layer to adsorb on the surface of a metal film by a spin coating method or a vapor deposition method are used for Raman and infrared spectroscopic analysis. The following method is described as an example in detail. This is a method of immersing the structure according to the present invention in an organic solution and then performing the Raman and infrared spectroscopic analysis.

An organic substance, that is, a dissolved substance, in the organic solution is desirably an organic substance which includes a functional group such as a thiol group or an amino group and has surface enhanced Raman activity or surface enhanced infrared activity. Deionized water or an organic solvent such as ethanol or ethylene glycol is desirably used as a solvent.

The amount of a sample adsorbed on the surfaces of the metal fine particles 14 or the surface of the metal film 18 by immersing the substrate according to the present invention in the organic solution depends on a combination of a metal element of the metal fine particles 14 or the metal fine particles 14 whose surfaces are covered with the metal film 18, a dissolved substance, a solvent, concentrations, and a solvent temperature. The concentration of the organic solution is desirably 0.001 mmol/L to 1 mol/L, particularly desirably 0.001 mmol/L to 1 mmol/L.

The amount of the sample adsorbed on the surfaces of the metal fine particles 14 or the surface of the metal film 18 by immersing the substrate according to the present invention in the organic solution also depends on the number of metal fine particles 14 or the number of metal fine particles 14 whose surfaces are covered with the metal film 18. In the case of Raman spectroscopic analysis, a spatial region of a point irradiated with laser light is a spherical region whose diameter is approximately 1 µm, so it is desirable to use the holes 17 with a depth equal to or smaller than 3 µm. In contrast to this, in the case of infrared spectroscopic analysis, for example, a region irradiated with infrared light when spectroscopic analysis is performed using a transmission method may be a region having a desirable size.

For example, a 0.1 mmol/L copper phthalocyanine (CuPc) aqueous solution (25° C. room temperature) is prepared. The base 13 in which Pd fine particles 14 or Pd fine particles 14 whose surfaces are covered with an Au film 18 are exposed is formed on the substrate 11 with the ground film 12. The resultant substrate is immersed in the aqueous solution for a necessary time. In this way, CuPc is adsorbed to the Pd fine particles 14 or the Au film 18. After that, the substrate is pulled up from the aqueous solution and subjected to ultrasonic cleaning with deionized water several times. Subsequently, the substrate is dried in a nitrogen atmosphere and then Raman and infrared spectroscopic analysis is performed.

The sample adsorbed at a thickness equal to or larger than the thickness of the monomolecular layer may be damaged in the case where the sample continues to be irradiated at a single point even with Raman laser light whose intensity is small. In order to prevent this, the sample desirably continues to be rotated.

In the structure according to the present invention, a large number of holes 17 are provided in the base 13 and the metal fine particles are exposed not only on the surface of the base 13 but also on the inner surfaces of the holes 17. As a result, a sample attached area is extremely wider than in the case where the holes 17 are not provided, so the detection sensitivity is improved. Even in the case of Raman laser light whose intensity is small or in the case of infrared light whose intensity is small, the spectroscopic analysis can be performed at high sensitivity. The metal fine particles 14 whose surfaces are covered with the metal film 18 are used, so the interspace distance between the metal fine particles 14 is reduced to 0 nm to 10 nm, with the result that the intensity of an electromagnetic field generated in the interspace is further increased to improve the detection sensitivity.

Next, an extension of life of the structure for supporting the sample to be subjected to surface enhanced vibrational spectroscopic analysis according to the present invention is described. Hereinafter, an example in which vibrational spectroscopic analysis is repeated several times using the same structure is described (see FIGS. 8A and 8B).

In order to perform spectroscopic analysis with the structure used for spectroscopic analysis at the same high sensitivity as in the case of a fresh structure, the following is required. In other words, it is necessary to remove inner curved surfaces of the holes 17 provided in the base 13.

A solution to be used for etching desirably has the following pH range. This is such a range pH that the sample attached to the metal fine particles 14, the metal fine particles 14, and the inner surfaces of the fine holes 17 provided in the base 13 (including the surfaces of the base 13) are dissolved. In particular, the solution desirably has an acid which is pH 2 to pH 6 or an alkali which is pH 10 to pH 14. A desirable example of the solution is a strong acid solution such as a phosphoric acid solution, a sulfuric acid solution, a hydrochloric acid solution, and a chromic acid solution, or a strong alkali solution such as a sodium hydroxide solution and ammonia water. However, the present invention is not particularly limited by the type of acid and the type of alkali. A mixture of several types of acid solutions or a mixture of several types of alkali solutions may be used. Etching conditions including a solution temperature, a concentration, and a time can be set as appropriate based on a state of the reused jig for vibrational spectroscopic analysis.

An example of desirable etching is that a jig for vibrational spectroscopic analysis (FIG. 8A) with which Raman spectroscopic analysis on copper phthalocyanine (CuPc) has been performed is immersed in a 1M NaOH aqueous solution for several minutes. Then, the diameter of the holes 17 before etching further increases to newly expose the Au fine particles 14 on the cross sections of the respective metal fine particle layers 15 which are located on the inner surfaces of the holes 17 (FIG. 8B).

When the jig for spectroscopic analysis to which no sample is attached is subjected to Raman spectroscopic analysis, Raman scattering from a substance other than the material of the jig for spectroscopic analysis is not observed. Subsequently, the jig for spectroscopic analysis is again immersed in a 0.1 mmol/L copper phthalocyanine (CuPc) aqueous solution for one minute and then subjected to ultrasonic cleaning with deionized water. After that, when the substrate (jig) is subjected to Raman spectroscopic analysis, the surface enhanced Raman scattered light intensity is increased higher than the result obtained by the first spectroscopic analysis.

In other words, the number of Au fine particles 14 exposed by the increase in diameter of the holes 17 is increased larger than that in the initial state. Therefore, the surface enhanced Raman scattered light intensity can be measured at higher sensitivity.

The diameter of the holes 17 is increased by repeating etching several times. Therefore, the number of exposed metal fine particles 14 increases, so the surface enhanced Raman scattered light intensity can be measured at higher sensitivity and the life of the structure lengthens.

EXAMPLES

Hereinafter, examples of the present invention are described. The present invention is not limited to the following examples.

Example 1

A Pd thin film 12 having a film thickness of 20 nm was formed as the ground film 12 on a Si substrate 11 by a sputtering method (FIG. 2A). An Au fine particle layer 15 (10 nm) and the Al layer 16 (30 nm) were continuously and alternately layered by a sputtering method to form a layered film 21 whose film thickness was 200 nm. An Au fine particle layer 15 having a film thickness of 5 nm was formed on the uppermost surface of the layered film 21, thereby producing a base 13 (FIG. 2B). Subsequently, the substrate was used as an anode and immersed in a 0.3 mol/L oxalic acid aqueous solution set at 16° C. Then, a voltage of 40 V was applied for anodic oxidation.

After the anodic oxidation, the sample was observed using a field emission scanning electron microscope (FE-SEM). As a result, holes 17 were formed in the layered film 21. The average diameter of the holes 17 was 30 nm and the center-to-center distance thereof was 50 nm. It was found that a large number of Au fine particles 14 having a particle size of 5 nm were exposed on the surface of the base 13 and on the cross sections of the respective metal fine particle layers 15 which are located on the inner surfaces of the holes 17 (FIG. 2C).

Next, the substrate was immersed in a 0.1 mmol/L copper phthalocyanine (CuPc) aqueous solution for one minute and then subjected to ultrasonic cleaning with deionized water. The substrate was subjected to morphological observation using an FE-SEM. As a result, CuPc was not observed on the Au fine particles. The substrate was subjected to Raman spectroscopic analysis. As a result, the SERS of CuPc was obtained.

Comparative Example 1

In Comparative Example 1, a Si substrate 11 with a Pd ground film 12 was prepared. An island-like gold film whose film thickness is approximately 20 nm was formed on the substrate 11 by vapor deposition of gold. The substrate 11 was immersed in a 0.1 mmol/L CuPc aqueous solution for one minute and then subjected to ultrasonic cleaning with deionized water. Subsequently, the sample was subjected to Raman spectroscopic analysis. As a result, Raman scattered light which is the SERS could be observed. The Raman scattered light intensity was approximately ⅙ of the intensity in Example 1.

Comparative Example 2

In Comparative Example 2, a substrate in which fine holes in an alumina layer formed by anodic oxidation are filled with Au is prepared (see US 2005/0105085). Fine holes having a fine hole diameter of 200 nm and a fine hole depth of 100 nm were formed in the alumina layer by anodic oxidation at an interval of 300 nm. The respective fine holes are filled with Au by electroplating. The plating continued even after the holes were filled with Au up to the height equal to the surface of the alumina layer. Therefore, the fine holes were buried with Au and the vicinities of the fine holes were excessively plated with Au. Thus, head portions of the Au fine particles were exposed and the interspace distance between the head portions of the Au fine particles was equal to or smaller than several nm. The diameter of the head portion of the Au fine particles was approximately 290 nm.

Subsequently, the substrate was immersed in a 0.1 mmol/L copper phthalocyanine (CuPc) aqueous solution for one minute and then subjected to ultrasonic cleaning with deionized water. Subsequently, Raman scattering spectroscopic analysis was performed. As a result, Raman scattering scattered light which is the SERS could be observed. The Raman scattered light intensity of the sample was reduced to approximately ½ of the intensity in Example 1.

(Result 1)

In Example 1, the number of Au fine particles 14 is larger than in Comparative Example 1, so the surface enhanced Raman scattered light intensity could be measured at higher sensitivity. In addition, in Example 1, the number of Au fine particles 14 and the number of interspaces between the adjacent Au fine particles 14 are larger than in Comparative Example 2, so the surface enhanced Raman scattered light intensity could be measured at higher sensitivity. This can be explained as follows. In Comparative Example 2, the Au fine particles 14 are two-dimensionally adjacent to one another. In contrast to this, the Au fine particles 14 in the present invention are three-dimensionally adjacent to one another. Thus, the number of interspaces between the adjacent Au fine particles 14 in the present invention is larger than in Comparative Example 2.

In Example 1, when thin film formation conditions such as the film thickness ratio between the metal fine particle layer 15 and the Al layer 16, and the number of layers thereof are controlled, the following can be performed. That is, it is possible to control the particle size of the metal fine particles 14, the dispersibility of the metal fine particles 14 (interspace distance between the metal fine particles), and the surface area of the fine holes 17. Therefore, the surface enhanced Raman scattered light intensity can be controlled as desired.

In Example 1, when anodic oxidation conditions such as the applied current, the type of the electrolytic solution used for anodic oxidation, and the electrolytic solution temperature are controlled, the surface area of the fine holes 17 can be adjusted to control the surface enhanced Raman scattered light intensity as desired.

Example 2

In this example, a Si layer is used instead of the Al layer 16 in Example 1.

A Pd thin film 12 having a film thickness of 20 nm was formed as the ground film 12 on a Si substrate 11 by a sputtering method (FIG. 2A). An Au fine particle layer 15 (10 nm) and an Si layer 16 (30 nm) were continuously and alternately layered by a sputtering method to form a layered film 21 whose film thickness was 200 nm. An Au fine particle layer 15 having a film thickness of 10 nm was formed on the uppermost surface of the layered film 21, thereby producing the base 13 (FIG. 2B). An Si target used for sputtering was of an n-type whose resistivity is 0.01 Ωcm to 0.03 Ωcm. Subsequently, the substrate was used as an anode and immersed in a mixture of hydrofluoric acid aqueous solution (5 w %) and ethanol aqueous solution (90 w %) which had a volume ratio of 1 (set at 25° C.). A current of 10 mA/cm² was applied for anodic oxidation. The sample was subjected to morphological observation using an FE-SEM. As a result, it was found that the large number of Au fine particles 14 having a particle size of 5 nm were exposed on the cross sections of the respective metal fine particle layers 15 which are located on the inner surfaces of the holes 17 having a hole diameter of 100 nm (FIG. 2C).

Next, the substrate was immersed in a 0.1 mmol/L copper phthalocyanine (CuPc) aqueous solution for one minute and then subjected to ultrasonic cleaning with deionized water. The substrate was subjected to morphological observation using an FE-SEM. As a result, CuPc was not observed on the Au fine particles 14. The substrate was subjected to Raman spectroscopic analysis. As a result, the SERS of CuPc was obtained.

Comparative Example 3

The measurement was performed in the same manner as in the case of Comparative Example 1. As a result, the intensity was approximately ⅕ of the intensity in Example 2.

Comparative Example 4

The measurement was performed in the same manner as in the case of Comparative Example 2. As a result, the intensity was approximately ⅗ of the intensity in Example 2.

(Result 2)

Such an effect difference may be caused by the same operation as described in Result 1.

Example 3

In this example, the following example are described (FIG. 1B and FIGS. 3A to 3D) A Si layer (base) 13 in which metal fine particles 14 are dispersed is formed on a ground film 12 provided on a substrate 11. After that, fine holes 17 are formed in the Si layer (base) 13 by anodic oxidation. The substrate 11 is immersed in a copper phthalocyanine aqueous solution and then subjected to Raman spectroscopic analysis.

A Pd thin film 12 having a film thickness of 20 nm was formed as the ground film 12 on the Si substrate 11 by a sputtering method (FIG. 3A). A metal fine particle layer 15 made of $Au_{0.4}Si_{0.6}$ (20 nm) and a Si layer 16 (30 nm) were alternately layered by a sputtering method to form a layered film 21. A metal fine particle layer 15 including a mixture of Au and Si and having a film thickness of 10 nm was formed on the uppermost surface of the layered film 21 (FIG. 3B). The total film thickness was 210 nm. The Si target used for sputtering was of an n-type whose resistivity is 0.01 Ωcm to 0.03 Ωcm. Then the substrate 11 was heated in an inert gas (Ar) atmosphere at an atmospheric pressure and 250° C. for 30 minutes (FIG. 3C).

Subsequently, the substrate was used as an anode and immersed in a mixture of hydrofluoric acid aqueous solution (5 w %) and ethanol aqueous solution (90 w %) which have a volume ratio of 1. The electrolytic solution temperature was set to a room temperature of 25° C. A current of 10 mA/cm² was applied for anodic oxidation (FIG. 3D). The sample was subjected to morphological observation using an FE-SEM. As a result, it was found that a large number of Au fine particles 14 were exposed on the entire inner surfaces of the holes 17 and on the entire surfaces of the base 13. The diameter of the holes 17 was 100 nm and a particle size of the Au fine particles 14 was 5 nm (FIG. 3C).

Next, the substrate was immersed in a 0.1 mmol/L copper phthalocyanine (CuPc) aqueous solution for one minute and then subjected to ultrasonic cleaning with deionized water. The substrate was subjected to morphological observation using an FE-SEM. As a result, CuPc was not observed on the Au fine particles 14. The substrate was subjected to Raman spectroscopic analysis. As a result, the SERS of CuPc was obtained. The Raman scattered light intensity of the sample was increased approximately 1.5 times the intensity in Example 2.

(Result 3)

As is apparent from the above description, the number of exposed Au fine particles 14 is larger than in Example 2, so the surface enhanced Raman scattered light intensity could be measured at higher sensitivity. This can be explained as follows. The metal fine particles are dispersed in the inner surfaces of the holes, so the number of metal fine particles exposed on the inner surfaces is increased, thereby increasing the number of molecules of the adsorbed sample as a matter of course.

In this example, when thin film formation conditions such as the film thickness ratio between the metal fine particle layer 15 including the mixture of Au and Si and the Si layer 16, the number of layers thereof, and the composition ratio between Au and Si, the heat treatment temperature and the heat treatment atmosphere are controlled, the following can be performed. That is, it is possible to control the particle size of the metal fine particles 14, the dispersibility of the metal fine particles 14 (interspace distance between the metal fine particles 14), and the surface area of the fine holes 17. Therefore, the surface enhanced Raman scattered light intensity can be controlled as desired.

In this example, when the conditions of the fine holes 17 formed by anodic oxidation, such as the applied current, the type of the electrolytic solution used for anodic oxidation, and the electrolytic solution temperature are controlled, the surface area of the fine holes 17 can be adjusted to control the surface enhanced Raman scattered light intensity as desired.

Example 4

In this example, a metal fine particle layer 15 and a (Al, Si) mixed layer 16 were alternately layered (FIG. 1A and FIGS. 4A to 4C).

An Au film having a film thickness of 20 nm was formed as a ground film 12 on a Si substrate 11 by a sputtering method (FIG. 4A). A (Al, Si) mixed layer 16 (25 nm) having a composition ratio Al: Si of 13:7 and an Au fine particle layer 15 (5 nm) were alternately layered by a sputtering method. Then, the Au fine particle layer 15 was formed at a film thickness of 5 nm. The total film thickness was 215 nm. The surface of the substrate was observed using an FE-SEM. As a result, a large number of columnar members 41 containing Al as a main ingredient were formed in the surfaces of the matrix portion 42 containing Si as main ingredient. The average diameter $2r$ was approximately 10 nm and the center-to-center distance $2R$ was approximately 15 nm. A large number of Au fine particles 14 having a particle size of 5 nm were formed on the surfaces of the columnar members 41 and the surfaces of the matrix portion 42. The cross section was observed. As a result, the columnar members 41 containing Al as a main ingredient were formed in the direction perpendicular to the surface of the substrate 11. The (Al, Si) mixed layers 16 and the Au fine particle layers 15 were alternately layered (FIG. 4B).

Next, the substrate was immersed for etching in a solution of phosphoric acid (5 wt %) set at 25° C. for two hours. The cross section of the substrate was observed using an FE-SEM. As a result, all the columnar members 41 containing Al as a main ingredient were dissolved to form holes 17. The average diameter $2r$ was approximately 10 nm and the center-to-center distance $2R$ was approximately 15 nm. The Au fine particles 14 each having a particle size of 5 nm were exposed in regions of the Au fine particles layer 15 on the inner surfaces of the holes 17 (FIG. 4C).

Next, the substrate was immersed in a 0.1 mmol/L copper phthalocyanine (CuPc) aqueous solution for one minute and then subjected to ultrasonic cleaning with deionized water. The substrate was subjected to morphological observation using an FE-SEM. As a result, CuPc was not observed on the surface of the exposed Au fine particles 14.

The substrate was subjected to Raman spectroscopic analysis. As a result, the SERS of CuPc was obtained. The Raman scattered light intensity of the sample was increased by approximately 2.5 times, compared with the intensity in Example 1.

(Result 4)

As is apparent from the above description, the number of fine holes 17 was increased to increase the number of exposed Au fine particles 14 larger than in Example 1, so the surface enhanced Raman scattered light intensity could be measured at higher sensitivity.

When various conditions are changed in this example, a desired light intensity can be obtained. Even in the case of infrared spectroscopic analysis, a surface enhanced infrared light intensity can be measured using a microscope reflection method in the same manner. This example can be applied to the case of the (Al, Ge) mixed layer and the case of the (Al, Si, Ge) mixed layer in the same manner. Therefore, the surface enhanced Raman scattered light intensity can be controlled as desired.

Example 5

In this example, an example in which the metal fine particles 14 are covered with a metal film 18 is described (FIGS. 7A and 7B).

A Pd thin film 12 having a film thickness of 20 nm was formed as a ground film 12 on a Si substrate 11 by a sputtering method. As in Example 1, a Pd fine particle layer 15 (10 nm) and an Al layer 16 (30 nm) were alternately layered by a sputtering method to form a layered film 21 whose film thickness was 200 nm. A Pd fine particle layer 15 was formed on the uppermost surface of the layered film 21 at a film thickness of 5 nm, thereby producing a base 13. Subsequently, the substrate 11 was used as an anode and immersed in a 0.3 mol/L oxalic acid aqueous solution set at 16° C. Then, a voltage of 40 V was applied for anodic oxidation.

After the anodic oxidation, the sample was observed using an FE-SEM. As a result, the holes 17 were formed in the Al layered film 21. The average diameter $2r$ was 30 nm and the center-to-center distance $2R$ was 50 nm. It was found that a large number of Pd fine particles 14 having a particle size of 5 nm were exposed on the surfaces of the base 13 and on regions of the respective Pd fine particle layers 15 which are located on the inner surfaces of the holes 17 (FIG. 7A).

Next, a gold nonelectrolytic plating bath was produced as a nonelectrolytic Au plating bath by mixing a 40 mL Dyn Gold AC-5R (produced by Daiwa Fine Chemicals Co., Ltd.), a 20 mL Dyn Gold M-20 (produced by Daiwa Fine Chemicals Co., Ltd.), and a 140 mL ion-exchange water. The nonelectrolytic Au plating bath was heated to be set at 75° C. The pH of the plating bath was 7.

With such a state, the manufactured substrate was immersed in the nonelectrolytic Au plating bath for one minute and then subjected to ultrasonic cleaning with deionized water. The sample was subjected to morphological observation. As a result, it was found that the Au film 18 having a film thickness of 10 nm were formed on the surfaces of the Pd fine particles 14 exposed on the inner surfaces of the holes 17 and on the surface of the base 13 and thus the inner surfaces of the holes 17 became more rough. In addition, the Au films 18 located on the respective Pd fine particles 14 were connected with each other or the interspace distance between the Pd fine particles 14 with the Au films 18 was reduced to several nm. An Au film having a film thickness of 10 nm was formed in the bottom portions of the holes 17 passing through the base 13 (on the ground film 12) (FIG. 7B).

Next, the substrate 11 was immersed in a 0.1 mmol/L copper phthalocyanine (CuPc) aqueous solution for one minute and then subjected to ultrasonic cleaning with deionized water. The substrate was subjected to morphological observation using an FE-SEM. As a result, CuPc was not observed on the Au films 18.

The substrate was subjected to Raman spectroscopic analysis. As a result, the SERS of CuPc was obtained. The Raman scattered light intensity of the sample was increased by approximately 1.5 times, compared with the intensity in Example 1.

(Result 5)

As is apparent from the above description, the Au film 18 was formed, so the surface roughness increased to strengthen the electromagnetic field in the interspace between the adjacent Pd fine particles 14 with the gold film 18, thereby improving the analysis sensitivity. Therefore, the surface enhanced Raman scattered light intensity could be measured at higher sensitivity.

When various conditions are changed in this example, a desired light intensity can be obtained. Even in the case of infrared spectroscopic analysis, a surface enhanced infrared light intensity can be measured using a transmission method or the like in the same manner. As in this example, the nonelectrolytic plating can be applied to Examples 2, 3, and 4.

Example 6

Figure 8A:
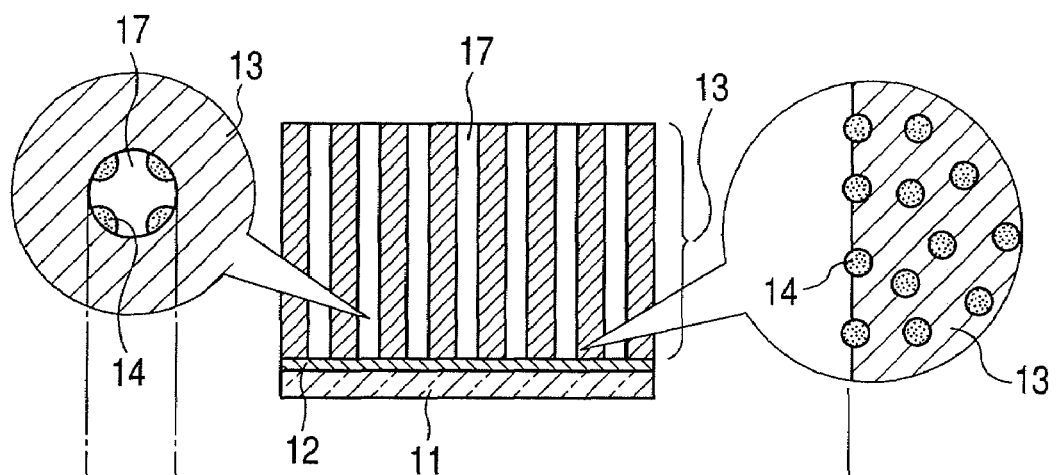
Figure 8B:
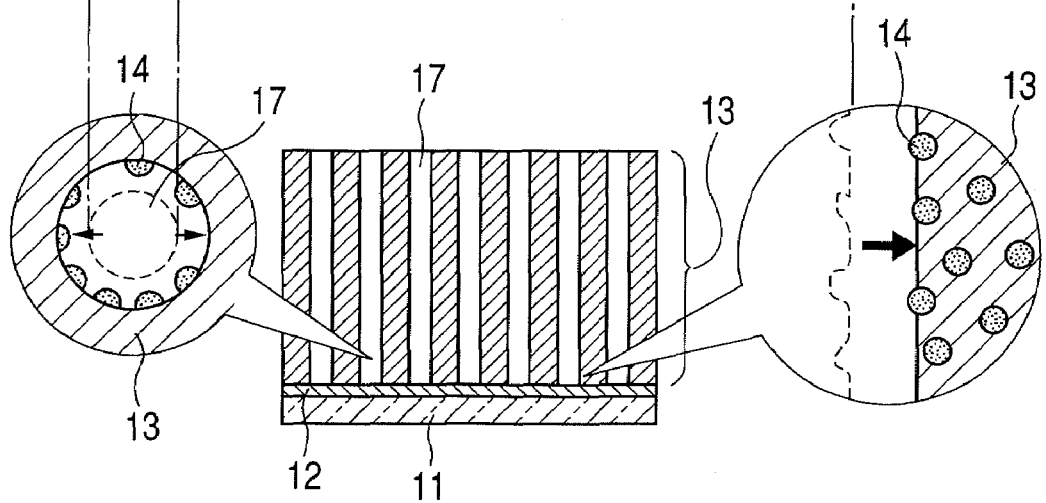

In this example, an example in which Raman spectroscopic analysis is performed one time and then Raman spectroscopic analysis is performed several times using the same jig again is described (FIGS. 8A and 8B).

The jig used for Raman spectroscopic analysis in Example 1 (FIG. 8A) was immersed for etching in a 1M NaOH aqueous solution for several minutes. Then, the jig was subjected to morphological observation using an FE-SEM. As a result, the diameter of the holes 17 was increased from 30 nm to 50 nm. It was found that the Au fine particles 14 were newly exposed on the cross sections of the respective metal fine particle layers 15 which are located on the inner surfaces of the holes 17 (FIG. 8B).

The jig was immersed in a 0.1 mmol copper phthalocyanine (CuPc) aqueous solution for one minute again and then subjected to ultrasonic cleaning with deionized water. After that, the jig was subjected to morphological observation using an FE-SEM. As a result, CuPc was not observed on the Au fine particles 14. The substrate (jig) was subjected to Raman spectroscopic analysis. As a result, the SERS of CuPc was obtained and the Raman scattered light intensity was increased by 10% of the intensity in Example 1.

(Result 6)

As is apparent from the above description, the diameter of the holes 17 was increased, so the number of exposed Au fine particles 14 was increased more than in Example 1. Therefore, the surface enhanced Raman scattered light intensity could be measured at higher sensitivity.

The diameter of the fine holes 17 is increased by repeating etching several times. Therefore, the number of exposed metal fine particles 14 increases, so the surface enhanced Raman scattered light intensity can be measured at higher sensitivity and the life of the jig for surface enhanced vibrational spectroscopic analysis lengthens. This can be applied to Examples 2, 3, and 4 and thus the lifetime can be lengthened.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2007-128268, filed May 14, 2007, which is hereby incorporated by reference herein in its entirety.

What is claimed is:

1. A structure for supporting a sample to be subjected to surface enhanced vibrational spectroscopic analysis, comprising:
   a substrate;
   a ground film formed on the substrate; and
   a base formed on the ground film,
   wherein the base includes a plurality of holes formed in a direction perpendicular to the substrate and metal fine particles are exposed on inner surfaces of the holes formed in the base and on a surface of the base,
   wherein the base is one of:
   a film in which a layer including metal fine particles and an Al layer are alternately layered;
   a film in which a layer including metal fine particles and an Si layer are alternately layered;
   an Si layer in which metal fine particles are dispersed; and
   a film in which a mixed layer including Al and at least one of Si and Ge and a layer including metal fine particles are alternately layered.

2. A structure according to claim 1, wherein the metal fine particles have an exposed portion covered with a metal film.

3. A structure according to claim 1, wherein the holes have a diameter of 1 nm to 1 μm, a center-to-center distance of 3 nm to 1.5 μm, and an aspect ratio equal to or larger than 2.

4. A structure according to claim 1, wherein the layer including the metal fine particles, the Al layer and the Si layer have a film thickness of 1 nm to 100 nm.

5. A structure according to claim 1, wherein the metal fine particles comprise a material selected from the group consisting of Au, Ag, Pd, Pt, and $M_xSi_{1-x}$, with $0 \leq X \leq 1$, M is one of Au, Ag, Pd, and Pt.

6. A structure according to claim 1, wherein the metal fine particles have a particle size of 1 nm to 30 nm, and an interspace distance of 0 nm to 100 nm.

7. A structure according to claim 2, wherein the metal film is comprised of either one of Au and Pt.

8. A structure according to claim 2, wherein the metal film has a film thickness of 1 nm to 30 nm.

9. A structure according to claim 1, wherein the ground film comprises a material selected from the group consisting of Au, Pd, and Pt.

10. A method of manufacturing a structure for supporting a sample to be subjected to surface enhanced vibrational spectroscopic analysis, at least comprising the steps of:
forming a ground film on a substrate;
forming, as a base, a film including metal fine particles on the ground film; and
forming a plurality of holes in the base in a direction perpendicular to the substrate;
wherein the metal fine particles are exposed on inner surfaces of the holes formed in the base and on a surface of the base by the step of forming the film and the step of forming the holes,
wherein the base is one of:
a film in which a layer including metal fine particles and an Al layer are alternately layered;
a film in which a layer including metal fine particles and an Si layer are alternately layered;
an Si layer in which metal fine particles are dispersed; and
a film in which a mixed layer including Al and at least one of Si and Ge and a layer including metal fine particles are alternately layered.

11. A method according to claim 10, further comprising the step of dispersing the metal fine particles by heat treatment after the step of forming the film including the metal fine particles.

12. A method according to claim 10, wherein the step of forming the holes in the base is performed using one of anodic oxidation and etching.

13. A method according to claim 10, further comprising the step of forming a metal film to cover the metal fine particles after the step of forming the holes.

14. A method according to claim 13, wherein the step of forming the metal film is performed using plating.

* * * * *